United States Patent
Stone et al.

(10) Patent No.: US 6,577,754 B2
(45) Date of Patent: Jun. 10, 2003

(54) ROBUST STAIN DETECTION AND QUANTIFICATION FOR HISTOLOGICAL SPECIMENS BASED ON A PHYSICAL MODEL FOR STAIN ABSORPTION

(75) Inventors: Ronald Stone, Pittsburgh, PA (US); Othman Abdulkarim, Pittsburgh, PA (US); Michael Fuhrman, Pittsburgh, PA (US)

(73) Assignee: TissueInformatics, Inc., Pittsburgh, PA (US)

( * ) Notice: Subject to any disclaimer, the term of this patent is extended or adjusted under 35 U.S.C. 154(b) by 0 days.

(21) Appl. No.: 10/158,486

(22) Filed: May 29, 2002

(65) Prior Publication Data

US 2002/0196964 A1 Dec. 26, 2002

Related U.S. Application Data

(60) Provisional application No. 60/294,097, filed on May 29, 2001.

(51) Int. Cl.[7] .................................................. G06K 9/00
(52) U.S. Cl. .................. 382/133; 382/128; 382/129; 382/133; 382/134; 600/309; 600/310; 600/317; 600/322; 600/442
(58) Field of Search .................................. 382/128, 129, 382/133, 134; 600/309, 310, 317, 322, 442

(56) References Cited

U.S. PATENT DOCUMENTS

| | | | | |
|---|---|---|---|---|
| 5,732,150 A | * | 3/1998 | Zhou et al. | 382/133 |
| 5,976,885 A | * | 11/1999 | Cohenford et al. | 436/63 |
| 5,991,028 A | * | 11/1999 | Cabib et al. | 356/456 |
| 6,165,734 A | * | 12/2000 | Garini et al. | 435/7.21 |
| 6,258,576 B1 | * | 7/2002 | Richards-Kortum et al. | 435/40.52 |

* cited by examiner

Primary Examiner—Andrew W. Johns
Assistant Examiner—Shervin Nakhjavan
(74) Attorney, Agent, or Firm—Louis M. Heidelberger; Lawrence B. Ebert; Nanda P. B. A. Kumar

(57) ABSTRACT

A physics based model of the absorption of light by histological stains used to measure the amount of one or more stains at locations within tissue is disclosed. The subsequent analysis results in several improvements in the detection of tissue on a slide, improvements to autofocus algorithms so focusing during image acquisition is confined to tissue, improvements to image segmentation and identification of tissued and its features, improvements to the identification of stain where multiple stains are used, and improvements to the quantification of the extent of staining. The invention relates to the application of these improvements to stain detection and quantification to provide for objective comparison between tissues and closer correlation between the presentations of such features and concurrent patterns of gene or protein expression.

7 Claims, 8 Drawing Sheets

ROBUST STAIN DETECTION AND QUANTIFICATION FOR HISTOLOGICAL SPECIMENS BASED ON A PHYSICAL MODEL FOR STAIN ABSORPTION

This application claims priority to application No. 60/294,097 filed May 29, 2001, and the text of application No. 60/294,097 is incorporated by reference in its entirety herewith.

FIELD OF THE INVENTION

The present invention generally relates to the processing of digital images of histopathological tissue specimens to provide for the objective characterization and analysis of tissue structural features ("tissue information"). Such tissue information allows for comparison and combination with tissue information obtained through studies taking place at different times, with different protocols for the collection, preservation and histological staining of the tissue. The present invention specifically relates to a system and method, based on a physical model for absorption of light by histological stains, to measure the amount of stain within specific locations within tissue.

BACKGROUND OF THE INVENTION

Generally, accurate and repeatable quantitative analysis of tissue is important to characterize the progression of various pathologies, and to evaluate effects that new therapies might have. To date, little, if any, reliable structural information exists at the tissue level (1–1000 microns, that is, in the range microscopic to mesoscopic). It is believed that if reliable, multi-dimensional tissue structural information existed in readily accessible databases capable of continuous assimilation with newly acquired information, including clinical and molecular (including genetic) information, such information would serve to enhance and accelerate new advances in tissue engineering, drug design and development, gene discovery, proteomics, and genomics research.

Specifically, this invention pertains to the improvement of methods of analysis of digital images of histopathological tissue specimens through the improved detection and interpretation of stains in such specimens. The development of an automated analysis system to identify and quantify structural features of tissues provides for objective comparison between tissues and allows for closer correlation between the presentations of such features and concurrent patterns of gene or protein expression.

There are several requirements for an automated analysis system. An automated system must be able to run un-attended for several hours. Slide feeding, slide positioning, tissue detection, auto-focus, and image acquisition, are all steps that must be accomplished before stain analysis can begin. This automated process mimics the manual process of capturing and saving tissue images by a pathologist. The technical hurdle in this step is to make this process robust even when histology and tissue placement are poor. This invention discloses a stain detection technique that enables the creation of a robust analysis system.

An example delineates the problem that is solved. Antibody staining is used to detect the presence of specific proteins in tissue, so that an improved method for detection and interpretation of stains in antibody staining helps researchers rapidly identify antibodies that may have potential as therapeutics. Specific antibody staining also locates structural features for objective classification and quantification, as where the CD31 antibody labels endothelial growth factors suggestive of new blood vessel formation. When horseradish peroxidase is used as a marker, the colored compound formed preferentially absorbs green and blue light with little absorption of red light. Where specific antibody staining of tissue occurs, it usually occurs to such a degree that the resulting image shows very strong absorption of green and blue light. The resulting observed color is dark reddish brown. In the areas where the tissue exhibits weak staining, the color varies over a range of light to dark reddish brown. Even if the tissue exhibits areas where staining is weak, this is not significant since the tissue has already been identified as showing specific staining because of the existence of the dark stained areas. As a result, the presence of specific staining can usually be detected by the existence of color within a small range of a single color. Specific stain is determined to exist within a tissue if a percentage of tissue has the color of dark specific staining and this percentage is above a user specified threshold value.

There is a problem if the tissue only exhibits weak specific staining. Non-specific staining exhibits a much smaller degree of staining, with the resulting image showing much less absorption of green and blue light. The resulting color is a light brown. The single color approach to specific stain detection may not work. Instead, the color that is an indication of specific staining can fall in a range between two colors, from dark reddish brown to light reddish brown. The problem then is to detect weak specific staining while rejecting non-specific staining and maintaining a low false positive detection rate.

The present invention overcomes the problems of the current art. Present visual/manual analysis of tissue is slow, difficult, prone to error, and subjective. Variability in specimen preparation and stain formulation reduces comparability among tissues or tissue sets through visual analysis or application of automated or computer-aided classifiers that apply an external reference for associating stain color with certain tissue components. The present invention describes how color information of a stained tissue image may be transformed to yield the type and amount of stain at each pixel of the stained tissue image. The present invention describes how statistically significant results may be obtained quickly.

SUMMARY OF THE INVENTION

The present invention is generally directed to the processing of digital images of histopathological tissue specimens to provide for the objective characterization and analysis of tissue structural features ("tissue information") by means of a robust automated analysis system. The development of a robust system to identify and quantify structural features of tissues provides for objective comparison between tissues and allows for closer correlation between the presentations of such features and concurrent patterns of gene or protein expression.

The present invention specifically discloses a physical model of stain absorption that relates the amount of stain present in an area of a stained histological specimen with the color and intensity of light transmitted through the specimen. This invention allows for improved automated detection of stained tissue areas as well as quantifications of the amount of stain present in each tissue area. Because the relative absorption of different stains is a means by which tissue structures are made visible, the disclosed computer-assisted detection of these stains facilitates the analysis of tissue structures.

In general aspects, the present invention is a method for analyzing the amount of stain on tissue specimens, which includes capturing an image of a tissue specimen. A background image is gathered from a region of a substrate (e.g., a microscopic slide used for mounting tissue sections) without any tissue mounts. A mean value in each band of a background image is calculated. Information from the background image to adjust the color image is used. A fixed number of points from the color image is randomly sampled.

Then, a principal component analysis to obtain three vectors are performed. Finally, the color image is transformed to a colorspace in which the colors of the colorspace show the type and amount of stain present.

The transmitted intensity of monochromatic light passing through an absorbing medium is measured by $I = I_0 \, e^{-\alpha s}$ where $I_0$ is the incident light intensity, a is known as the absorption coefficient of the absorbing medium, and s is the product of the concentration of the dye in a stained specimen (medium) and the thickness of the tissue containing a given stain(s) that the light passes through.

In one aspect, the present invention is a method for analyzing the amount of stain on tissue specimens, which includes the steps of capturing an image of a stained tissue specimen; gathering a background image from a substrate used for supporting tissue specimens; calculating a mean value in each band of a background image; randomly sampling a fixed number of points from the color image; performing a principal component analysis to obtain three vectors; and transforming the color image to a colorspace in which the colors of the colorspace show the type and amount of stain present.

In staining reactions, dyes (hematoxylin and/or eosin (for H&E stain) may be dissolved in the stained substance. A dye may be absorbed on the surface of a structure (e.g., antibody) or dyes may be precipitated within the structure depending on pH, temperature etc of staining solution. Color may vary with specific staining solutions used. A substance that is stained by the basic dye ((e.g., H&E dyes) is basophilic. A staining solution containing hematoxylin and eosin dyes is one such staining solution.

In another aspect, a method for analyzing the amount of stain on tissue specimens includes the steps of capturing an image of a stained tissue specimen; transforming the color image to a colorspace representation in which points are represented by triplets of numbers comprising intensities of red, green, and blue colors; defining a stain curve defined in terms of a light source and a certain point in the color image; calculating the distance in colorspace along the stain curve from the triplet representing the light source to the triplet representing the certain point; and calculating the amount of stain.

In still another aspect, a method for analyzing the amount of stain on tissue specimens includes the steps of capturing a color image of a tissue specimen; forming a three-dimensional colorspace describing the color image; performing a principal component analysis on the three-dimensional colorspace; using the results of the principal component analysis to form a transformation matrix; and calculating the amount of stain by using the transformation matrix.

In yet another aspect, a method for analyzing the amount of stain on tissue specimens includes the steps of staining a tissue specimen; creating a colored image of the tissue specimen, wherein the image is comprised of pixels, wherein each pixel comprises a red, green and blue sub-pixel, wherein each sub-pixel has an intensity and the intensities of each pixel define a triple of intensity values; gathering a background image; converting the triple of intensity values into a triple of optical density values; randomly sampling the optical density values to obtain a number of values large enough to obtain statistically significant results; performing a principal component analysis on the randomly sampled optical density values to obtain a new coordinate system; and using the new coordinate system to define a transformation matrix to convert the triple of optical density values into a triple of values, wherein a component of the triple of values is proportional to the amount of stain at that point.

In still another aspect, a method for analyzing the amount of stain on tissue specimens includes the steps of staining a tissue specimen such that a feature of the tissue specimen is stained; creating a colored image of the tissue specimen, wherein the image is comprised of pixels, wherein each pixel comprises a red, green and blue sub-pixel, wherein each sub-pixel has an intensity and the intensities of each pixel define a triple of intensity values; gathering a background image; converting the triple of intensity values into a triple optical density values; randomly sampling the optical density values to obtain a number of values large enough to obtain statistically significant results; performing a principal component analysis on the randomly sampled optical density values to obtain a new coordinate system; and using the new coordinate system to define a transformation matrix to convert the triple of optical density values into a triple of values, wherein a component of the triple of values is proportional to the amount of stain at that point and wherein the amount of stain at that point is proportional to the amount of the tissue feature.

In a further aspect, a method for analyzing the amount of stain on tissue specimens includes the steps of staining a tissue specimen with two stains, a first stain and a second stain; creating a colored image of the tissue specimen, wherein the image is comprised of pixels, wherein each pixel comprises a red, green and blue sub-pixel, wherein each sub-pixel has an intensity and the intensities of each pixel define a triple of intensity values;

converting the triple of intensity values into a triple of difference values linearly related to the amount of stains; randomly sampling the difference values to obtain a number of values large enough to obtain statistically significant results; performing a principal component analysis on the randomly sampled difference values to obtain a new coordinate system; and using the new coordinate system to define a transformation matrix to convert the triple of difference values into a triple of values, wherein one component of the triple of values is proportional to the amount of the first stain at that point and a second component of the triple of values is proportional to the amount of the second stain at that point.

In another aspect, a method for analyzing the amount of stains on tissue specimens wherein there are three stains on a stained tissue specimen. This method includes the steps of staining a tissue specimen with three stains, a first stain, a second stain, and a third stain; creating a colored image of the tissue specimen, wherein the image is comprised of pixels, wherein each pixel comprises a red, green and blue sub-pixel, wherein each sub-pixel has an intensity and the intensities of each pixel define a triple of intensity values; gathering a background image; using a filter to filter out the color of the third stain; converting the triple of intensity values into a triple of difference values linearly related to the amount of stains; randomly sampling the difference values to obtain a number of values large enough to obtain statistically significant results; performing a principal component analysis on the randomly sampled difference values to obtain a new coordinate system; and using the new coordinate system to define a transformation matrix to convert the triple of difference values into a triple of values, wherein one component of the triple of values is proportional to the amount of the first stain at that point and a second component of the triple of values is proportional to the amount of the second stain at that point.

DETAILED DESCRIPTION OF THE INVENTION

Generally, the present invention represents a novel approach to an automated measurement and analysis system to quantitatively evaluate tissues while reducing the uncertainty, imprecision, time, and subjectivity involved in making manual measurements. The present invention is directed to a robust database that is based upon input parameters that may be uniformly investigated and extracted from different studies. The present invention is directed to a database that allows input and retrieval of data and images needed to compare studies taking place at different times, with different protocols, and with measurements made by different systems. The present invention is directed to a database which preserves the utility of the stored information through continued lossless combination and comparability with subsequently acquired information and the accessibility of the stored images for automated re-analysis.

Specifically, this invention describes a physics based model of the absorption of light by histological stains in order to measure the amount of stain at locations within tissue. The subsequent analysis results in several improvements in the detection of tissue on a slide, improvements to autofocus algorithms so focusing during image acquisition is confined to tissue, improvements to image segmentation and identification of tissued and its features, improvements to the identification of stain where multiple stains are used, and improvements to the quantification of the extent of staining. This invention discloses the application of these improvements to stain detection and quantification to the detection of specific antibody staining.

The physical model of stain absorption relates the amount of stain present in an area of a stained histological specimen with the color and intensity of light transmitted through the specimen. This allows for improved detection of stained tissue areas as well as determinations of the amount of stain present in each tissue area. These improvements, in turn, allow for improvements in the detection of tissue in digital images, which impacts the speed of auto-focus algorithms. Since the relative absorption of different stains is the means by which tissue structures are made visible, the computer-assisted detection of these structures is facilitated. Finally, for digital images of tissues that were stained with a smaller number of stains than the number of color bands in the image, quantification of the amount of staining at every point in the image can allow for basic image compression.

Figure 1:
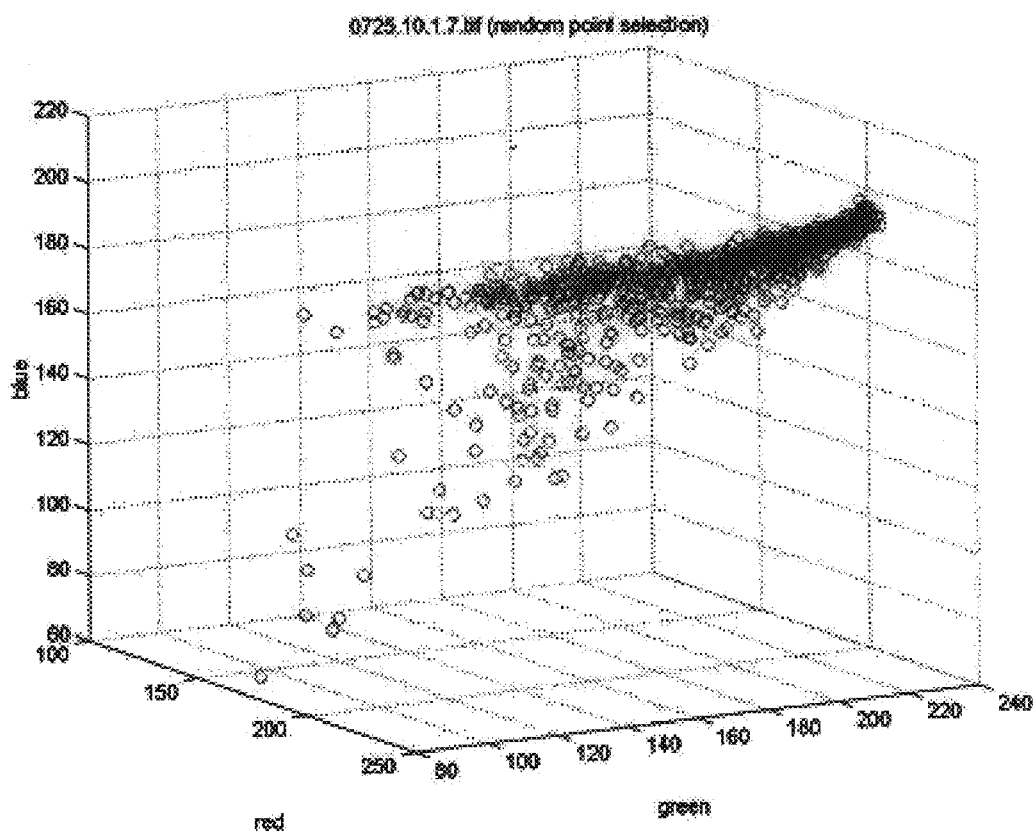
FIG. 1. A colorspace (intensity) representation showing the colorspace distribution of pixels sampled from an image.

The invention is more easily understood in terms of the following comments. Every pixel in a digital color image has assigned to it an intensity in each of several color bands. For most color images, there are three (red, green, and blue) color bands. (Without loss of generality, we will assume in further discussions that there are three color bands unless noted otherwise.) Thus, the three values for each pixel may be plotted in a three dimensional space, called colorspace, to yield an alternative description of an image. FIG. 1 shows a plot of some of the pixels in an image.

In order to perform a thresholding operation on an image, it is necessary to define a volume in this colorspace, and to divide pixels into two classes—those whose triplet of colorspace values falls within the defined volume, and those whose colorspace triplet lies outside it. It is common to define the volume as a sphere or parallelepiped with axes parallel to the axes of the colorspace. It is possible, however, to take into account the physical process by which the image is formed in order to determine the organization of the points in colorspace and improve upon image thresholding. Consider a small area of stained tissue, having only a single type of stain. Let the colorspace triplet for the microscope light source be $(I_{0r}, I_{0g}, I_{0b})$. (This is, therefore, also the triplet for the "background", or non-tissue areas in the digital image of the tissue as seen through the microscope.) As light passes through the tissue area, it will be attenuated by the stain, with greater amounts of stain producing greater attenuation. Thus, the colorspace triplets of points having different amounts of stain will lie along a curve in colorspace which starts at the triplet representing the background, or light source, and likely ends at the position of no transmitted light, or (0,0,0). The equation of this curve is not known presently, but likely follows either exponential or linear attenuation. For exponential attenuation, in which increased staining occurs by stain building up on top of previously laid down stain, a point (triplet) on the curve, denoted $(I_r, I_g, I_b)$ is given $$(I_r, I_g, I_b) = (I_{0r} e^{-\alpha_r s}, I_{0g} e^{-\alpha_g s}, I_{0b} e^{-\alpha_b s}) \tag{1}$$

where $\alpha_r$, $\alpha_g$, and $\alpha_b$ are attenuation coefficients for each band, and x is the amount of stain present. For linear attenuation, in which increased staining occurs when stain covers a larger percentage of the tissue area, a point (triplet) on the curve is given by $$(I_r, I_g, I_b) = (I_{0r}[1-\alpha_r s], I_{0g}[1-\alpha_g s], I_{0b}[1-\alpha_b s]) \tag{2}$$

Figure 2:
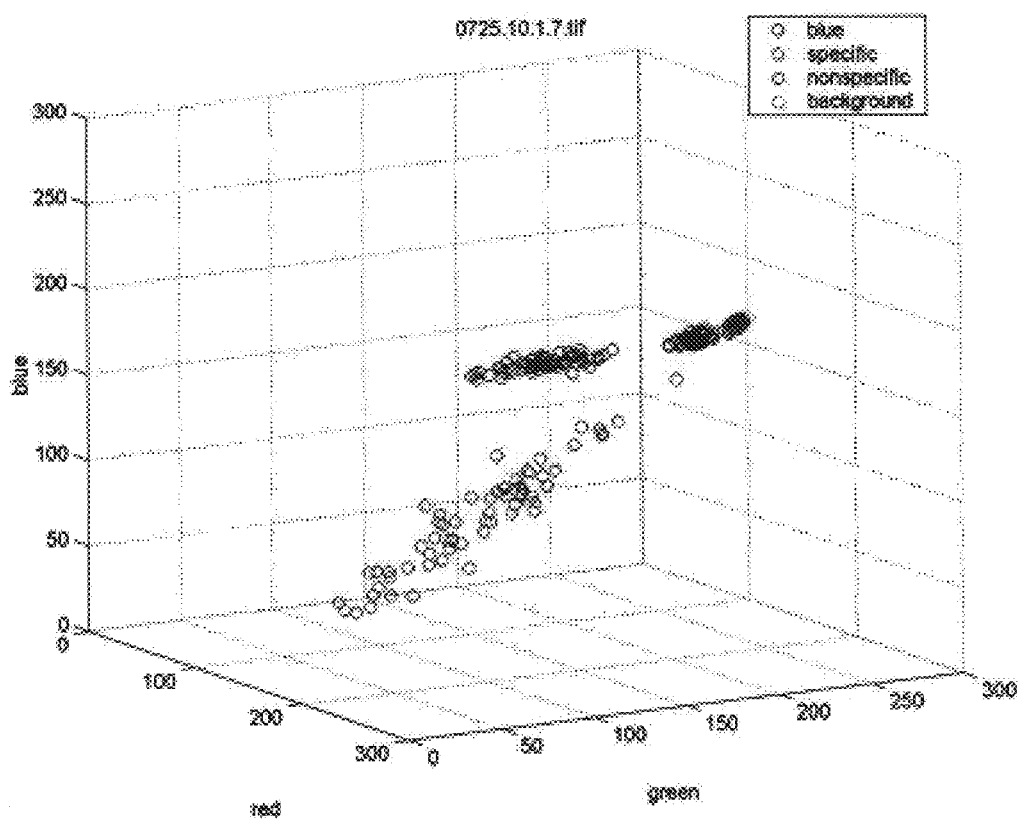
FIG. 2. A colorspace (intensity) representation of points selected from a color image of an immunohistochemically-stained tissue having two stains.

For each stain present in a tissue section, there is a separate curve in colorspace. For example, FIG. 2 shows points sampled from an image of immunohistochemically-stained tissue having two stains.

The colorspace triplet for each point on the tissue will be the sum of the colorspace triplets for each stain present in the tissue at that point. Each additional stain yields an additional curve in colorspace, and there is theoretically no limit to the number of stains that may be applied.

Figure 3:
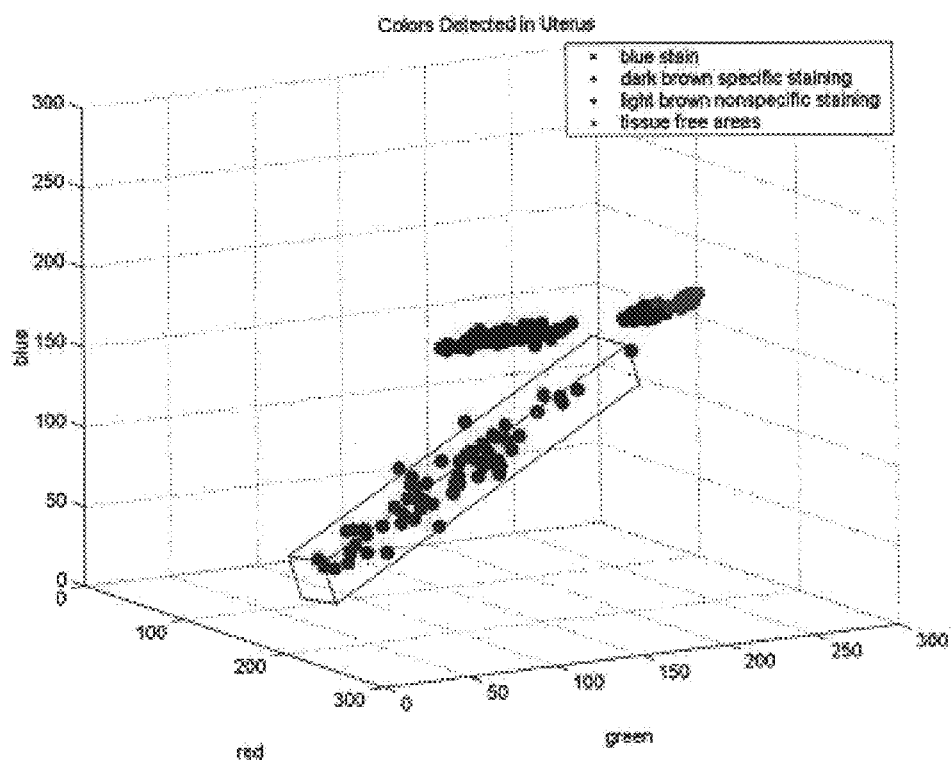
FIG. 3. A colorspace (intensity) representation comprising a volume with a square cross-section drawn around a curve representing different amounts of one of the stains present in the tissue under study.

The physical description of the formation of images of stained histological specimens allows for more accurate detection of staining. While common methods of stain detection will apply a threshold to an image by defining a sphere or parallelepiped with sides parallel to the colorspace axes, as noted above, use of the physically-based model will allow for the choice of more appropriate volumes. For example, in FIG. 3, a volume with a square cross-section has been drawn around the curve representing different amounts of one of the stains present in the tissue under study. This volume can be determined automatically in a way that compensates for variations in histology.

This ability to address variability in the preparation of a histopathological tissue specimen specifically distinguishes this invention from existing methods of processing tissue images for analysis. In the presence of such variability, the automated comparison of objective measures of the features or structural characteristics of the tissue is impaired. A fixed reference for classifying the presence of stain at a particular location on the tissue will arbitrarily exclude relevant features of tissues to which stain has been poorly applied.

This ability to clearly define the regions in colorspace that represent the color of a particular stain also allows measurement of the amount of stain at any point in the image, a task which is difficult by other methods. The amount of stain present at any point in the tissue can be determined by calculating the distance in colorspace along the stain curve from the triplet representing the light source to the triplet representing the point in question. The amount of stain can then be calculated by using equation 1 or 2. Estimates of biological parameters can then be inferred from the amount of stain present. The most important biological parameters that benefit from this analysis are obviously the features the stain is meant to enhance and for which it is applied. Thus, for example, the ability to accurately detect hematoxylin will improve the ability to detect nuclei in H&E-stained tissue sections, the ability to accurately measure the amount of staining by acid fuchsin, which is used in the van Gieson staining protocol, will improve the ability to detect collagen in Verhoeff-van Gieson-stained tissue sections, or the ability to detect CD31 antibody staining will improve the ability to locate and measure new blood vessel formation for the study of aniogenesis.

The ability to model the appearance of stain in digital images also improves the functioning of other image processing algorithms, most importantly auto-focus and image compression. One of the most difficult aspects of auto-focus algorithms is the determination of whether an image contains regions of tissue or not, since such algorithms will fail on images which contain no tissue or other features. It is common practice to attempt to determine the presence of tissue in an image by studying the histograms of pixel intensity for each band of the image. This method, however, has the same shortcomings as the usual methods for applying a threshold. The ability to better determine the appearance of stain in an image, and thus accurately determine if an image contains any tissue from its colorspace representation, can prevent the failure of auto-focus algorithms.

The model can also aid in image compression. If there are two stains used on a tissue, then all the points in the colorspace representation must lie in a plane, if there are three stains, all points must lie in a hyperplane of three dimensions, and so on. If new colorspace axes are chosen to lie along the colorspace stain curves, then an image may be represented with as many color bands as there are stains. Thus, for instance, an image of an H&E-stained tissue section, which has two stains, may be represented with two color bands, rather than the usual three of red, green, and blue. This compresses the image to ⅔ its original size.

Details of Embodiments

According to the Beer-Lambert Law of Absorbance, which is only approximately correct, the transmitted intensity of monochromatic light passing through an absorbing medium is given by $$I = I_0 e^{-\alpha s}$$

where $I_0$ is the incident light intensity, $\alpha$ is known as the absorption coefficient of the absorbing medium, and s is the product of the concentration of the absorbing medium and path length. The Beer-Lambert Law holds for every wavelength of incident light, with a different value of a for every wavelength. Thus, for an imaging device with N bands, the Beer-Lambert Law may be written as $$(I_1, I_2, I_3, \ldots, I_N) = (I_{01}e^{-\alpha_1 s}, I_{02}e^{-\alpha_2 s}, I_{03}e^{-\alpha_3 s}, \ldots, I_{0N}e^{-\alpha_N s})$$

where $I_{0j}$ is the incident light intensity in band j, and $\alpha_j$ is the absorption coefficient in band j. If there are multiple absorbing media (multiple stains in the case of histologically prepared tissue specimens), the absorbance effects are multiplicative. So, for example, in the case of two stains, the transmitted intensity is $$(I_1, I_2, I_3, \ldots, I_N) = ($$
$$I_{01}e^{-\alpha_1 s} \cdot e^{-\beta_1 t}, I_{02}e^{-\alpha_2 s} \cdot e^{-\beta_2 t}, I_{03}e^{-\alpha_3 s} \cdot e^{-\beta_3 t}, \ldots, I_{0N}e^{-\alpha_N s} \cdot e^{-\beta_N t}) =$$
$$(I_{01}e^{-(\alpha_1 s + \beta_1 t)}, I_{02}e^{-(\alpha_2 s + \beta_2 t)}, I_{03}e^{-(\alpha_3 s + \beta_3 t)}, \ldots, I_{0N}e^{-(\alpha_N s + \beta_N t)})$$

where the β values are the absorption coefficients for the second stain, and t is product of the concentration and path length for the second stain.

To facilitate further calculations, the optical density may be calculated. If $D_j$ denotes the optical density in band j, the optical density is given by $$(D_1, D_2, D_3, \ldots, D_N) = -(\ln[I_1/I_{01}], \ln[I_2/I_{02}], \ln[I_3/I_{03}], \ldots, \ln[I_N/I_{0N}])$$

Thus, for the example of the case of two stains, the optical density is $$(D_1, D_2, D_3, \ldots, D_N) = ([\alpha_1 s + \beta_1 t], [\alpha_2 s + \beta_2 t], [\alpha_3 s + \beta_3 t], \ldots, [\alpha_N s + \beta_N t]) = s(\alpha_1, \alpha_2, \alpha_3, \ldots, \alpha_N) + t(\beta_1, \beta_2, \beta_3, \ldots, \beta_3 N)$$

For an image of histologically prepared tissue with two stains, the α values and β values are constant for a given choice of two stains, but the values of s and t may vary from one pixel location to the next as the concentrations of the stains and the path length vary. Thus, the values of optical density calculated from the image must lie in a plane in the space of all possible optical density values.

From this knowledge of the behavior of the transmitted light intensity in an image of a histologically prepared and stained tissue specimen, it is possible to produce an image that shows the amount of each type of stain (the product of the concentration and path length) present at each pixel location. For clarity, we describe the case of two stains, although the method need not be limited to this case.

The following is one method, but not the only method, by which to utilize the optical density description of staining and image formation.

1. The optical density (in each band) at every point in the image is calculated by dividing the value of each pixel in the image by the value of the corresponding pixel in the background image and by then taking the negative of the natural logarithm of this value. In equation form this is:

$$(D_r, D_g, D_b) = (-\ln(r/r_0), -\ln(g/g_0), -\ln(b/b_0))$$

where $(D_r, D_g, D_b)$ are the optical densities in the red, green, and blue channels, respectively, at a pixel. In the same way, r, g, and b are the values in the red, green, and blue channels, respectively, at the pixel, and $r_0$, $g_0$, and $b_0$ are the values in the red, green, and blue channels, respectively, of the corresponding pixel in the background image. [One can refer to the red, green, and blue channels as sub-pixels.]

Figure 4:
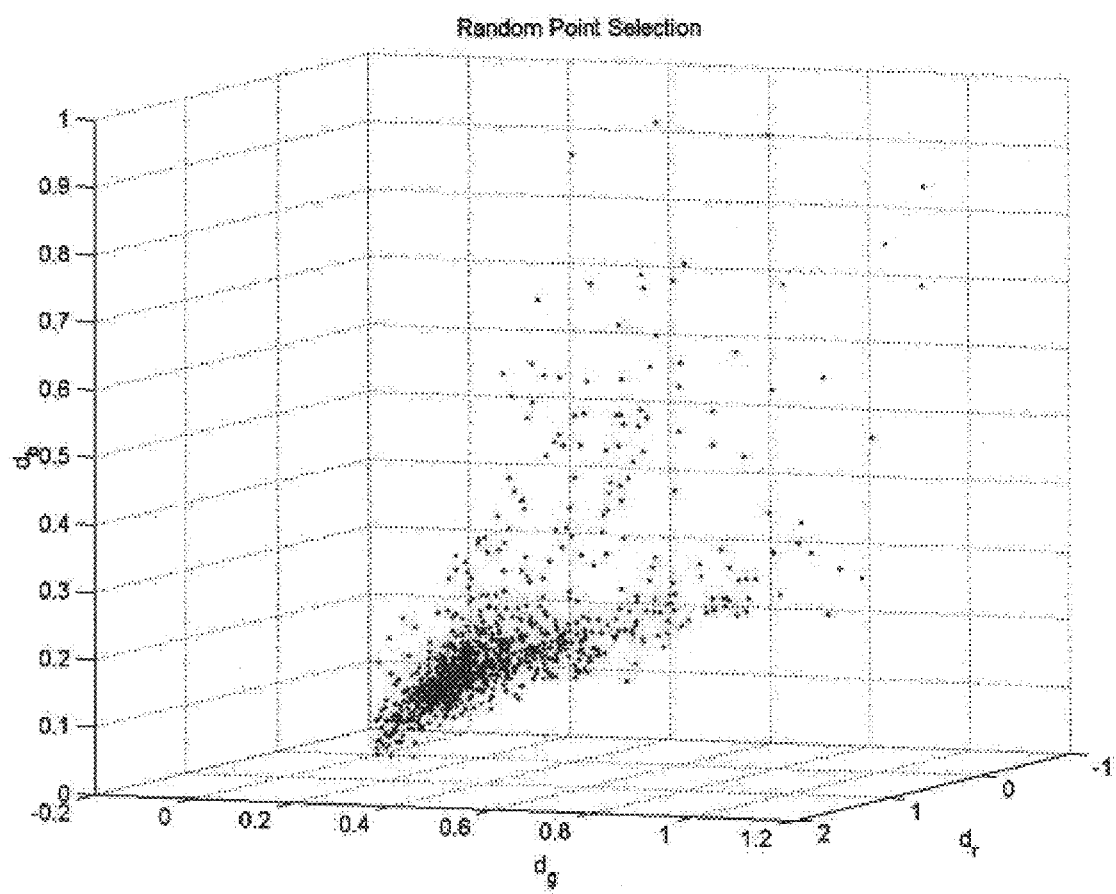
FIG. 4. A graph of optical density (absorbance) triplets of the randomly selected points.
Figure 5:
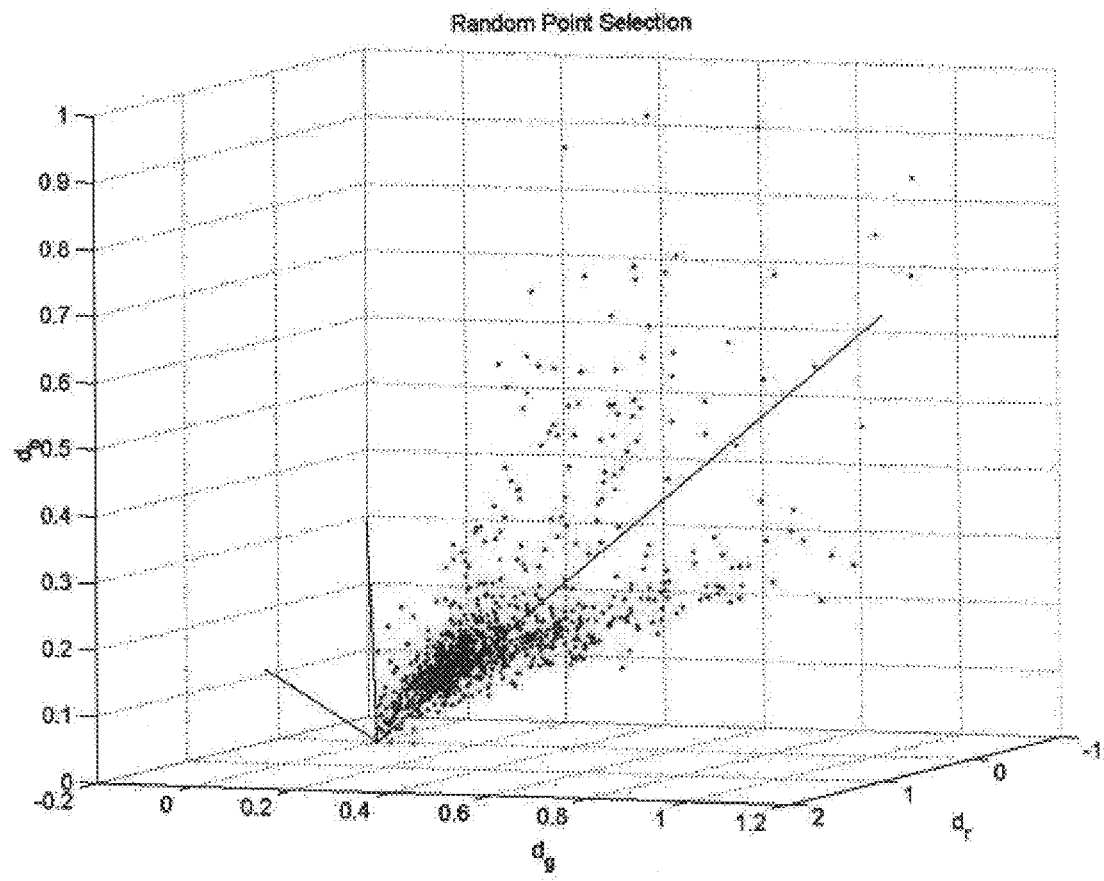
FIG. 5. A graph of the vectors along the principal directions superimposed on the distribution of optical density (absorbance) triplets.

2. A fixed number of points are randomly sampled from the resultant optical density image, and their $(D_r, D_g, D_b)$ triplets are recorded. The number of points sampled must be large enough to yield statistically significant results but should be small enough for the calculations to proceed quickly. Commonly, one thousand points are sampled. FIG. 4 shows a graph of the $(D_r, D_g, D^b)$ triplets of the randomly selected points. The points are distributed in a roughly triangular planar region, with an apex of the triangle being located at (0 0 0).

3. A Principal Component Analysis is performed on the sampled points. This yields three vectors, or principal components, and associated scalars known as principal values. The principal component with the largest principal value lies along the best-fit line to the distribution, the two components with the two largest principal values define the best-fit plane to the distribution, and the principal component with the smallest principal value is the perpendicular to the best-fit plane. FIG. 2 shows vectors along the principal directions superimposed on the distribution of optical density triplets.

4. All of the triplets in the distribution are projected onto the second-largest principal component. The resulting values are sorted.

5. The value that is larger than a given percentage of all the projections is found and is denoted $x_1$; the value that is smaller than a given percentage of all the projections is found and is denoted $x_2$. For instance, $x_1$ and $x_2$ may be set such that 95% of the projected values are less than $x_1$ and 95% of the values are greater than $x_2$.

6. The triplets that, upon projection, produced the values $x_1$ and $x_2$ are found. These triplets are denoted $P_1=(D_{r1}, D_{g1}, D_{b1})$ and $P_2=(D_{r2}, D_{g2}, D_{b2})$.

7. The projections of these triplets onto the largest principal component are found.

8. From these projections onto the first- and second-largest principal components, it is possible to find the projections of $P_1$ and $P_2$ onto the best-fit plane. The triplets of the projections onto the best-fit plane are denoted $P_3=(D_{r3}, D_{g3}, D_{b3})$ and $P_4=(D_{r4}, D_{g4}, D_{b4})$.

9. The unit vectors from the origin to $P_3$ and $P_4$ are calculated. These unit vectors are denoted $v_1$ and $v_2$, and they represent an approximation to the curve in the optical density space for each of the two pure stains present in the image.

Figure 6:
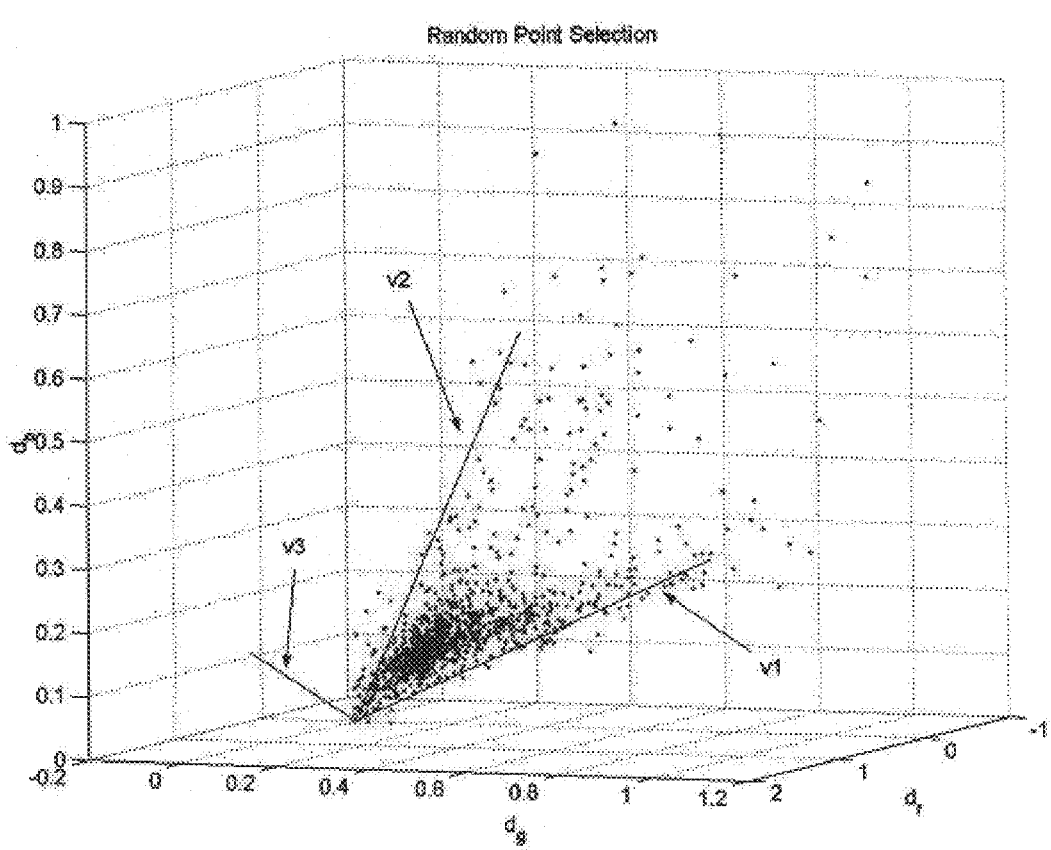
FIG. 6. A graph of the vectors parallel to the new coordinate system basis vectors superimposed on the distribution of the sampled points.

10. A new coordinate system is defined by $v_1$, $v_2$, and $v_3$, where $v_3$ is the unit vector in the direction of the smallest principal component, and $v_1$, $v_2$, and $v_3$ form a right-handed coordinate system. FIG. 6 shows vectors parallel to the new coordinate system basis vectors superimposed on the distribution of the sampled points.

11. The basis vectors of the original optical density space, i.e. the unit vectors along the $D_r$, $D_g$, and $D_b$ directions, are denoted $v_r$, $v_g$, and $v_b$. The transformation matrix, $M=$

| | | |
|---|---|---|
| $v_1 \cdot v_r$ | $v_1 \cdot v_g$ | $v_1 \cdot v_b$ |
| $v_2 \cdot v_r$ | $v_2 \cdot v_g$ | $v_2 \cdot v_b$ |
| $v_3 \cdot v_r$ | $v_3 \cdot v_g$ | $v_3 \cdot v_b$ | is formed. The notation $v_1 \cdot v_r$ indicates the vector dot product between $v_1$ and $v_r$.

12. For every point in the optical density image generated in step 1, its triplet, $(D_r, D_g, D_b)$, is found, and it is transformed according to $$(a, b, c) = (D_r, D_g, D_b) M^{-1}$$

and the original triplet, $(D_r, D_g, D_b)$ is replaced by the new triplet $(a, b, c)$. The first and second channels of the resultant image each contain information about one of the two stains present in the original image, and the third band contains noise. The value in a given channel at a point is proportional to the amount of stain of the type represented by that channel that is present at that point.

It is possible to approximate the Beer-Lambert Law as $$I = I_0 e^{-\alpha s} \approx I_0 [1 - \alpha s]$$

For the case of two stains, this yields $$(I_1, I_2, I_3, \ldots, I_N) = ($$
$$I_{01} e^{-(\alpha_1 s + \beta_1 t)},$$
$$I_{02} e^{-(\alpha_2 s + \beta_2 t)},$$
$$I_{03} e^{-(\alpha_3 s + \beta_3 t)}, \ldots, I_{0N} e^{-(\alpha_N s + \beta_N t)}) \approx (I_{01}[1 - \alpha_1 s - \beta_1 t], I_{02}[1 - \alpha_2 s - \beta_2 t], I_{03}[1 - \alpha_3 s - \beta_3 t], \ldots, I_{0N}[1 - \alpha_N s - \beta_N t])$$

The less of the absorbing medium is present, the more accurately this approximation holds. This approximation allows for a less computationally expensive calculation of the optical density. Moreover, because of the linear relationship between the incident intensity and transmitted intensity, a calculation analogous to that performed for optical densities may be performed directly on the intensities. In this case, $$(I_{01}-I_1, I_{02}-I_2, I_{03}-I_3, \ldots, I_{0N}-I_N) =$$
$$(I_{01}[\alpha_1 s + \beta_1 t], I_{02}[\alpha_2 s + \beta_2 t], I_{03}[\alpha_3 s + \beta_3 t], \ldots, I_{0N}[\alpha_N s + \beta_N t]) = s(I_{01}\alpha_1, I_{02}\alpha_2, I_{03}\alpha_3, \ldots, I_{0N}\alpha_N) + t(I_{01}\beta_1, I_{02}\beta_2, I_{03}\beta_3, \ldots, I_{0N}\beta_N)$$

If the incident intensities for each band are approximately equal, as would be the case with incident light that is near-white in color, and which is the case for most transmission microscopy applications, this equation reduces to $$(I_{01}-I_1, I_{02}-I_2, I_{03}-I_3, \ldots, I_{0N}-I_N) = sI_0(\alpha_1, \alpha_2, \alpha_3, \ldots, \alpha_N) + tI_0(\beta_1, \beta_2, \beta_3, \ldots, \beta_N)$$

The following calculations then parallel those in the optical density case.

The following is one method, but not the only method, by which to utilize the approximate, intensity-based description of staining and image formation.

Figure 7:
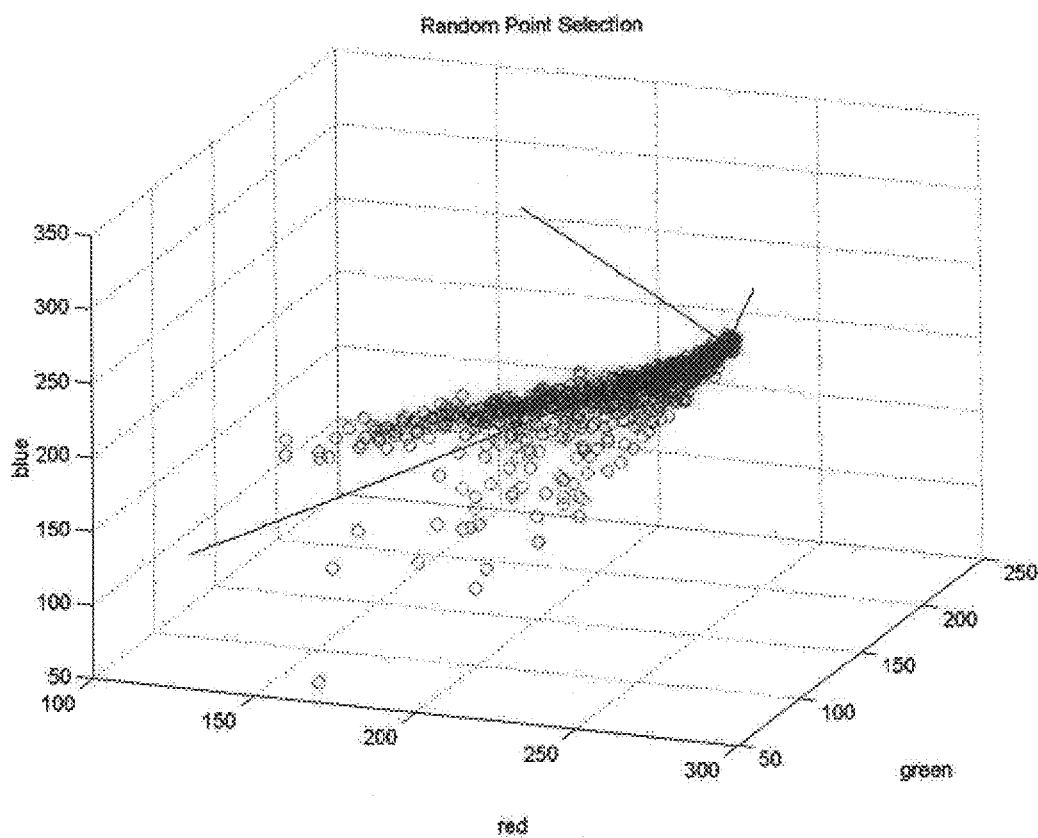
FIG. 7. A colorspace (intensity) representation showing the distribution of colorspace triplets and vectors along the principal component directions, and illustrating the two largest vectors (represented by the longer straight lines) defining the best-fit plane of the distribution.
Figure 8:
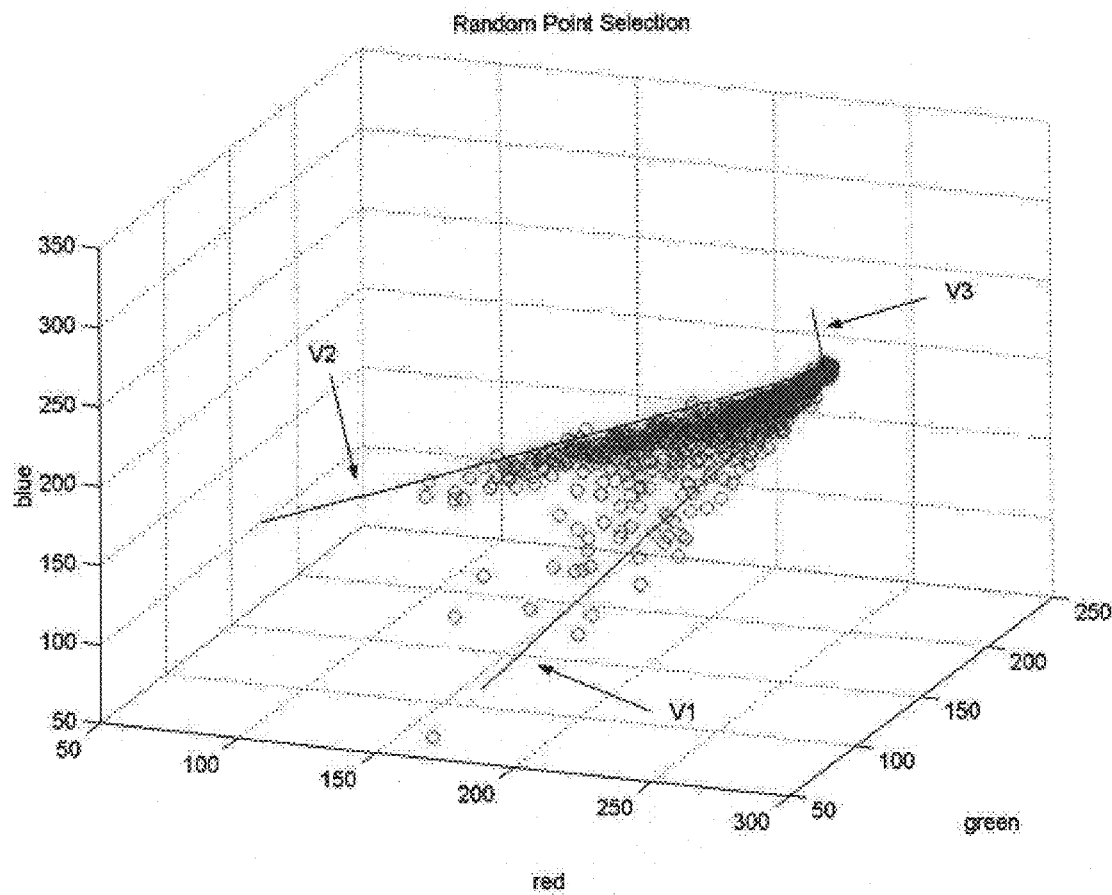
FIG. 8. A colorspace (intensity) representation showing the colorspace distribution of the sampled pixels, and illustrating the new coordinate system basis vectors, $v_1$, $v_2$, and $v_3$.

13. The mean value in each band of the background image is calculated and stored as a colorspace triplet. This triplet is denoted $(r_0, g_0, b_0)$.
14. A fixed number of points are randomly sampled from the image under study, and their colorspace triplets, denoted $(r, g, b)$, are recorded. The number of points sampled must be large enough to yield statistically significant results but should be small enough for the calculations to proceed quickly. Commonly, one thousand points are sampled. FIG. 1 shows the randomly sampled points plotted in colorspace. The mean colorspace triplet for the background image is at (234, 218, 201), near the apex of the triangular cloud of points.
15. For every sampled point, the quantity $(r_0-r, g_0-g, b_0-b)$ is calculated.
16. A Principal Component Analysis is performed on the distribution of these values. This yields three vectors, or principal components, and associated scalars known as principal values. The principal component with the largest principal value lies along the best-fit line to the distribution, the two components with the two largest principal values define the best-fit plane to the distribution, and the principal component with the smallest principal value is the perpendicular to the best-fit plane. In order to convert back to the original colorspace, the value $(r_0, g_0, b_0)$ is added to each principal component. FIG. 7 shows the distribution of colorspace triplets and vectors along the principal component directions.
17. All of the triplets in the distribution are projected onto the second-largest principal component. The resulting values are sorted.
18. The value that is larger than a given percentage of all the projections is found and is denoted $x_1$; the value that is smaller than a given percentage of all the projections is found and is denoted $x_2$. For instance, $x_1$ and $x_2$ may be set such that 95% of the projected values are less than $x_1$ and 95% of the values are greater than $x_2$.
19. The colorspace triplets that, upon projection, produced the values $x_1$ and $x_2$ are found. These triplets are denoted $P_1=(r_1, g_1, b_1)$ and $P_2=(r_2, g_2, b_2)$.
20. The projections of these triplets onto the largest principal component are found.
21. From these projections onto the first- and second-largest principal components, it is possible to find the projections of $P_1$ and $P_2$ onto the best-fit plane. The triplets of the projections onto the best-fit plane are denoted $P_3=(r_3, g_3, b_3)$ and $P_4=(r_4, g_4, b_4)$.
22. The unit vectors from the colorspace triplet of the background mean to $P_3$ and $P_4$ are calculated. These unit vectors are denoted $v_1$ and $v_2$, and they represent an approximation to the colorspace curve for each of the two stains present in the image.
23. A new coordinate system is defined by $v_1$, $v_2$, and $v_3$, where $v_3$ is the unit vector in the direction of the smallest principal component. FIG. 8 shows the colorspace distribution of the sampled points and vectors parallel to the new coordinate system basis vectors.
24. The basis vectors of the original colorspace are denoted $v_r$, $v_g$, and $v_b$. The transformation matrix, M=

| $v_1 \cdot v_r$ | $v_1 \cdot v_g$ | $v_1 \cdot v_b$ |
| $v_2 \cdot v_r$ | $v_2 \cdot v_g$ | $v_2 \cdot v_b$ |
| $v_3 \cdot v_r$ | $v_3 \cdot v_g$ | $v_3 \cdot v_b$ | is formed.

25. For every point in the image, its colorspace triplet, $(r, g, b)$, is found, and it is transformed according to $(a, b, c) = (r, g, b)M^{-1}$, and the original colorspace triplet, $(r, g, b)$ is replaced by the new colorspace triplet $(a, b, c)$. The colors of the image now show the type and approximately the amount of stain present at each pixel.

Features of the Invention

The present invention differs from the prior art in many ways. An embodiment of the present invention begins with an image of a stained tissue and a background image. ["background image" can be the portion of the image without tissue. One can define the background image in terms of bands, which are ranges of wavelengths. For example, one could define the background image in terms of red, green and blue bands, and calculate a mean background intensity for each band.] For every point of the image of the stained tissue, the optical density or difference in intensity from the mean background intensity is calculated. A large number of points in the image from different areas of the tissue sample are selected. A principal component analysis is performed to find the directions that best describe these sampled points. The first principal component lies long the best fit line to the distribution of points, or the longest axis of the distribution. The next largest principal component is perpendicular to the first and lies long the next largest axis of the distribution. A preferred embodiment of the present invention does not use these principal components as the final output, but rather uses these components as a means to obtain amounts of tissue features, which are themselves proportional to amounts of stain. In this preferred embodiment, the amount of each stain present at each point in the tissue specimen is quantified. From the principal components and the distribution of points, this preferred embodiment allows one to determine the vectors in optical density space along which pure stain of each type lies. From these vectors, it is possible to determine how much stain of each type is present at any chosen point in the tissue. This can be done because the optical density and color of any point in the image of the tissue is determined entirely the amount of each stain present at that point, and each optical density and color can result from only one combination of the amounts of the two stains. Then, for every point in the image, the embodied method allows calculation of how much of each stain is present in the tissue at that point. The embodied method allows creation of a new image in which the first band, say for example the red band, shows the amount of stain of the first type, and the second band, say for example the green band, shows the amount of stain of the second type. The more stain present at a point, the brighter the output image at that point. Thus, for a pixel in the input image of a point in the tissue that has a large amount of stain of the first type and almost no stain of the second type, the corresponding pixel in the output image will appear bright red. For a pixel in the input image of a point in the tissue with a small amount of both types of stain, the corresponding pixel in the output image will appear as dim yellow, and for a pixel in the input image of a pint in the tissue that has neither stain present, the output image will appear black. In this case, any blue present in the image is just noise and can be eliminated.

The Present Invention Has Other Features.
1. There are embodiments for both the Beer-Lambert law and the linear approximation to it.
2. There are embodiments which use the principal components and other methods to calculate the lines in optical density space which represent the curves of the optical density of the pure stains.
3. There are embodiments which permit one to use the calculated lines for pure stain in optical density space to form a transformation matrix from stain space to optical density space.
4. There are embodiments which invert the matrix to find the transformation from optical density space to stain space.
5. There are embodiments which permit one to transform every pixel in the optical density image into stain space, resulting in a stain space image, in which the individual bands of the image give the amounts of individual stains in the tissue.

What is claimed is:
1. A method for analyzing the amount of stain on tissue specimens, comprising the steps of
    capturing a color image of a tissue specimen;
    transforming the color image to a colorspace representation in which points are represented by triplets of numbers comprising intensities of red, green, and blue colors;
    defining a stain curve defined in terms of a light source and a certain point in the color image;
    calculating the distance in colorspace along the stain curve from the triplet representing the light source to the triplet representing the certain point; and
    calculating the amount of stain.
2. The method of claim 1, wherein the stain is from a hematoxylin dye containing solution.
3. The method of claim 1 wherein the stain is from hematoxylin and eosin dyes containing solution.

4. A method for measuring the amount of stain on a stained tissue specimen, comprising the steps of
    staining a tissue specimen;
    creating a colored image of the tissue specimen, wherein the image is comprised of pixels, wherein each pixel comprises a red, green and blue sub-pixel, wherein each sub-pixel has an intensity and the intensities of each pixel define a triple of intensity values;
    gathering a background image;
    converting the triple of intensity values into a triple of optical density values;
    randomly sampling the optical density values to obtain a number of values large enough to obtain statistically significant results;
    performing a principal component analysis on the randomly sampled optical density values to obtain a new coordinate system; and
    using the new coordinate system to define a transformation matrix to convert the triple of optical density values into a triple of values, wherein a component of the triple of values is proportional to the amount of stain at that point.

5. A method for measuring the amount of tissue feature on a stained tissue specimen, comprising the steps of
    staining a tissue specimen such that a feature of the tissue specimen is stained;
    creating a colored image of the tissue specimen, wherein the image is comprised of pixels, wherein each pixel comprises a red, green and blue sub-pixel, wherein each sub-pixel has an intensity and the intensities of each pixel define a triple of intensity values;
    gathering a background image;
    converting the triple of intensity values into a triple optical density values;
    randomly sampling the optical density values to obtain a number of values large enough to obtain statistically significant results;
    performing a principal component analysis on the randomly sampled optical density values to obtain a new coordinate system; and
    using the new coordinate system to define a transformation matrix to convert the triple of optical density values into a triple of values, wherein a component of the triple of values is proportional to the amount of stain at that point and wherein the amount of stain at that point is proportional to the amount of the tissue feature.

6. A method for measuring the amount of two stains on a stained tissue specimen, comprising the steps of
    staining a tissue specimen with two stains, a first stain and a second stain;
    creating a colored image of the tissue specimen, wherein the image is comprised of pixels, wherein each pixel comprises a red, green and blue sub-pixel, wherein each sub-pixel has an intensity and the intensities of each pixel define a triple of intensity values;
    converting the triple of intensity values into a triple of difference values linearly related to the amount of stains;
    randomly sampling the difference values to obtain a number of values large enough to obtain statistically significant results;
    performing a principal component analysis on the randomly sampled difference values to obtain a new coordinate system; and using the new coordinate system to define a transformation matrix to convert the triple of difference values into a triple of values, wherein one component of the triple of values is proportional to the amount of the first stain at that point and a second component of the triple of values is proportional to the amount of the second stain at that point.

7. A method for measuring the amount of stains wherein there are three stains on a stained tissue specimen, comprising the steps of staining a tissue specimen with three stains, a first stain, a second stain, and a third stain;

creating a colored image of the tissue specimen, wherein the image is comprised of pixels, wherein each pixel comprises a red, green and blue sub-pixel, wherein each sub-pixel has an intensity and the intensities of each pixel define a triple of intensity values;

gathering a background image;

using a filter to filter out the color of the third stain;

converting the triple of intensity values into a triple of difference values linearly related to the amount of stains;

randomly sampling the difference values to obtain a number of values large enough to obtain statistically significant results;

performing a principal component analysis on the randomly sampled difference values to obtain a new coordinate system; and using the new coordinate system to define a transformation matrix to convert the triple of difference values into a triple of values, wherein one component of the triple of values is proportional to the amount of the first stain at that point and a second component of the triple of values is proportional to the amount of the second stain at that point.

* * * * *